(12) United States Patent
Brown et al.

(10) Patent No.: US 8,012,456 B2
(45) Date of Patent: Sep. 6, 2011

(54) BIOLOGICAL MODELS CAPABLE OF EXHIBITING SECONDARY DISEASE MANIFESTATIONS AND USEFUL FOR DEVELOPING THERAPEUTIC DRUGS, DIAGNOSTIC PRODUCTS AND THERAPEUTIC OR DIAGNOSTIC PROCEDURES, METHODS OF USING SAME, AND CELLS, TISSUES AND ORGANS DERIVED THEREFROM

(75) Inventors: Jennifer June Brown, Bronx, NY (US); Elazar Rabbani, New York, NY (US); James J. Donegan, Long Beach, NY (US); Jayanta Roy-Chowdhury, New Rochelle, NY (US)

(73) Assignee: Enzo Therapeutics, Inc., Farmingdale, NY (US)

(*) Notice: Subject to any disclaimer, the term of this patent is extended or adjusted under 35 U.S.C. 154(b) by 0 days.

(21) Appl. No.: 10/042,711

(22) Filed: Dec. 12, 2001

(65) Prior Publication Data

US 2003/0150000 A1     Aug. 7, 2003

Related U.S. Application Data

(63) Continuation-in-part of application No. 08/876,635, filed on Jun. 16, 1997, now abandoned.

(51) Int. Cl.
   *A61K 49/00* (2006.01)
   *A01K 67/00* (2006.01)
   *A01K 67/033* (2006.01)
(52) U.S. Cl. .................. 424/9.1; 424/9.2; 800/8; 800/9
(58) Field of Classification Search .................. 800/8, 9, 800/10, 11, 12, 13; 435/325, 1.1; 424/9.1, 424/9.2
   See application file for complete search history.

(56) References Cited

U.S. PATENT DOCUMENTS 5,580,776 A   12/1996   Wilson et al.
5,709,843 A    1/1998   Reisner

OTHER PUBLICATIONS

Agy et al. (1992) Infection of Macaca nemestrina by human immunodeficiency virus type-1. Science 257: 103-106.*
Barnett et al. (1994) An AIDS-Like condition induced in baboons by HIV-2. Science 266: 642-646.*
Kuby, J. (1991) Immunology, 2nd Edition. (W.H. Freeman and Company, New York) pp. 496-497.*
Lewis et al. (1995) Developing animal models for AIDS research—progress and problems. Trends in Biotechnology 13: 142-150.*
Mosier et al. (1991) Human immunodeficiency virus infection of human-PBL-SCID mice. Science 251: 791-794.*
Namikawa et al. (1988) Infection of the SCID-hu mouse by HIV-1. Science 242: 1684-1686.*
Walter et al. (1996) Hepatitis B infection of Tupaia hepatocytes in vitro and in vivo. Hepatology 24(1): 1-5.*
Yan et al. (1992) Human hepatitis B virus and hepatocellular carcinoma I. Experimental infection of tree shrews with hepatitis B virus. J. Cancer Research and Clin. Oncology 122: 283-288.*
Xie et al. (1998) Transmission of hepatitis C virus infection to tree shrews. Virology 244: 513-520.*
Yan et al. (1996) Human hepatitis B virus and hepatocellular carcinoma. II. Experimental induction of hepatocellular carcinoma in tree shrews exposed to hepatitis B virus and aflatoxin B1. J. Cancer Res. Clin. Oncol. 122: 289-295.*
Liu, D., et al., "Stable Human Immunodeficiency Virus Type 1 (HIV-1) Resistance in Transformed CD4 + Monocytic Cells Treated with Multitargeting HIV-1 Antisense Sequences Incorporated into U1 snRNA," *J. Virol.* 71:4079-4085 (1997).
Shibata, R., et al., "Early replication block of human immunodeficiency virus type 1 in monkey cells," *J. Gen. Virol.* 76:2723-2730 (1995).
Bowling, W.M., et al., "Portal Branch Occlusion Safely Facilitates in Vivo Retroviral Vector Transduction of Rat Liver," *Human Gene Therapy* 7:2113-2121 (1996).
Engelhardt, J., et al., "Direct gene transfer of human CFTR into human bronchial epithelia of xenografts with E1-deleted adenoviruses," *Nature Genetics* 4:27-33 (1993).
Kim, T.S., et al., "Immunity to B16 melanoma in mice immunized with IL-2-secreting allogeneic mouse fibroblasts expressing melanoma-associated antigens," *Int. J. Cancer* 51:283-289 (1992).
McCune, J.M., et al., "The SCID-hu Mouse: Murine Model for the Analysis of Human Hematolymphoid Differentiation and Function," *Science* 241:1632-1639 (1988).
Orkin, S.H., and Motulsky, A.G., "Report and recommendations of the panel to assess the NIH investment in research on gene therapy," NIH Ad-Hoc Committee Report, Dec. 7, 1995.
Rhim, J.A., et al., "Complete reconstitution of mouse liver with xenogeneic hepatocytes," *Proc. Natl. Acad. Sci. USA* 92:4942-4946 (1995).
Weber, M., et al., "Adenoviral Transfection of Isolated Pancreatic Islets: A Study of Programmed Cell Death (Apoptosis) and Islet Function," *J. Surgical Res.* 69:23-32 (1997).

* cited by examiner

*Primary Examiner* — Anne-Marie Falk
(74) *Attorney, Agent, or Firm* — Natalie Bogdanos, Esq.; Elie Gendloff, Esq.

(57) ABSTRACT

This invention provides novel animal models for a human pathogen that is capable of exhibiting analogous secondary disease manifestation. Other animal models for a human pathogen are provided by this invention which are capable of exhibiting analogous secondary disease manifestations and are also capable of responding to therapeutic or preventive measures to such secondary disease manifestations. Other animal models for human retrovirus infections are provided including lower primates and primate excluding any members of the order Anthropoidea. Compositions, drugs, products and procedures for therapeutic and diagnostic applications derived from the animal models of this invention are also described and provided.

2 Claims, 6 Drawing Sheets

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 1
tgcctgagtg cwgtatg                                                17
```

```
<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 2
taggaggctg taggcat                                                          17

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Probe

<400> SEQUENCE: 3
tttataaggg tcgatgtcca t                                                     21
```

BIOLOGICAL MODELS CAPABLE OF EXHIBITING SECONDARY DISEASE MANIFESTATIONS AND USEFUL FOR DEVELOPING THERAPEUTIC DRUGS, DIAGNOSTIC PRODUCTS AND THERAPEUTIC OR DIAGNOSTIC PROCEDURES, METHODS OF USING SAME, AND CELLS, TISSUES AND ORGANS DERIVED THEREFROM

REFERENCE TO RELATED PATENT APPLICATIONS

This application is a continuation-in-part of U.S. patent application Ser. No. 08/876,635, filed on Jun. 16, 1997, now abandoned, the contents of which application are fully incorporated by reference herein.

FIELD OF THE INVENTION

This invention relates to the field of animal models including lower primate and primate excluding the order anthropoidae. Such models are useful for developing therapeutic drugs, diagnostic products, and the like, as well as therapeutic and diagnostic processes. This invention also relates to methods of using these animal models, and further includes cells, tissues and organs derived therefrom.

All patents, patent applications, patent publications, scientific articles, and the like, cited or identified in this application are hereby incorporated by reference in their entirety in order to describe more fully the state of the art to which the present invention pertains.

BACKGROUND OF THE INVENTION

When a pathogen is able to infect a particular host there are varying levels of susceptibility. The subsequent infection may be transient in nature or it may continue to be a chronic infection. The pathogen may be cytopathic or non-cytopathic in the host organism. There may also be secondary manifestations of the infection that are not directly related to propagative processes of the pathogens themselves. For instance, a cytopathic virus can kill cells directly, but a non-cytopathic virus can indirectly kill cells by inducing a host immune response that is responsible for death of the infected cell. Other secondary manifestations can include inflammation, fibrosis, induced auto-immunity, apoptosis and cancer.

Due to the specific nature of some pathogens towards their host, there is a keen lack of appropriate animal model systems for testing therapeutic regimens for preventing, stabilizing or reversing some human disease manifestations. The art is also limited by the fact that in some systems, although there may be proliferation of the pathogen within the animal subject, the course of illness may be different from what is seen in a human subject. Presumably in these cases, the environment of the animal model is sufficiently different that key features of the disease seen in humans are not expressed. On the other hand and in contrast, there may be unique biological manifestations in the surrogate animal that are not seen in humans.

For instance, in cases where the host is not the natural host of a pathogen, the pathogen may be able to infect the cells or organs of the host but not be able to proliferate. An example of this would be HIV infection of macaques. Infection of these animals by the human virus HIV leads to low or unreproducible infection which is believed to be caused by a specific block in replication (Shibata et al., 1995, J Gen Virol; 76:2723). On the other hand, some viruses have a broad range of suitable hosts that can carry active infections from one species to another with rabies virus being a noted example. Although disease may be caused by replication of a pathogen, there may be other indirect or secondary manifestations that can be host specific. For instance, both humans and chimpanzees are able to be productively infected by HIV but the course of disease presentation is widely different between the two species since the chimpanzees lack the secondary manifestations that are expressed after infection of humans.

HBV is a pathogen that has been associated with secondary manifestations in humans. HBV has been shown to be able to infect a primitive primate, *Tupaia belangeri*, (Yan et al., 1996, described in related Ser. No. 08/876,635, filed on Jun. 16, 1997) but the correspondence of this infection with the disease process seen in humans has not been clear. Walter et al., 1996, also described in Ser. No. 08/876,635, reported that HBV infection of *Tupaia* is not analogous to the human disease in that there was only a very short, transient production of viral antigens without any evidence of chronic infection. Thus, the latter teaches away from the use of *Tupaia* as animal model systems that are analogous to infections of humans by HBV.

The limitations and disadvantages in the prior art field of animal models described above are overcome by the present invention as described below.

SUMMARY OF THE INVENTION

The present invention uniquely provides a non-chimpanzee animal model for a human pathogen. This animal is extremely useful because it is capable of exhibiting analogous secondary disease manifestation.

The present invention further provides an animal model for a human pathogen that is both capable of exhibiting analogous secondary disease manifestation and is capable of responding to therapeutic or preventive measures in said animal model to the secondary disease manifestation.

This invention also provides a lower primate as an animal model for human retrovirus infections, including such retrovirus infections as Human Immunodeficiency Virus (HIV) and Human Lymphotrophic T-cell Leukemia (HTLV).

Also provided by this invention is a primate as an animal model for human retrovirus infections, such a primate excluding any members of the Anthropoidea.

Other useful therapeutic drugs and products, diagnostic products, therapeutic and diagnostic procedures, and cells, tissues and organs derived from any other animal models of this invention, are also provided by this invention, as further described and exemplified below.

DETAILED DESCRIPTION OF THE INVENTION

Figure 1:
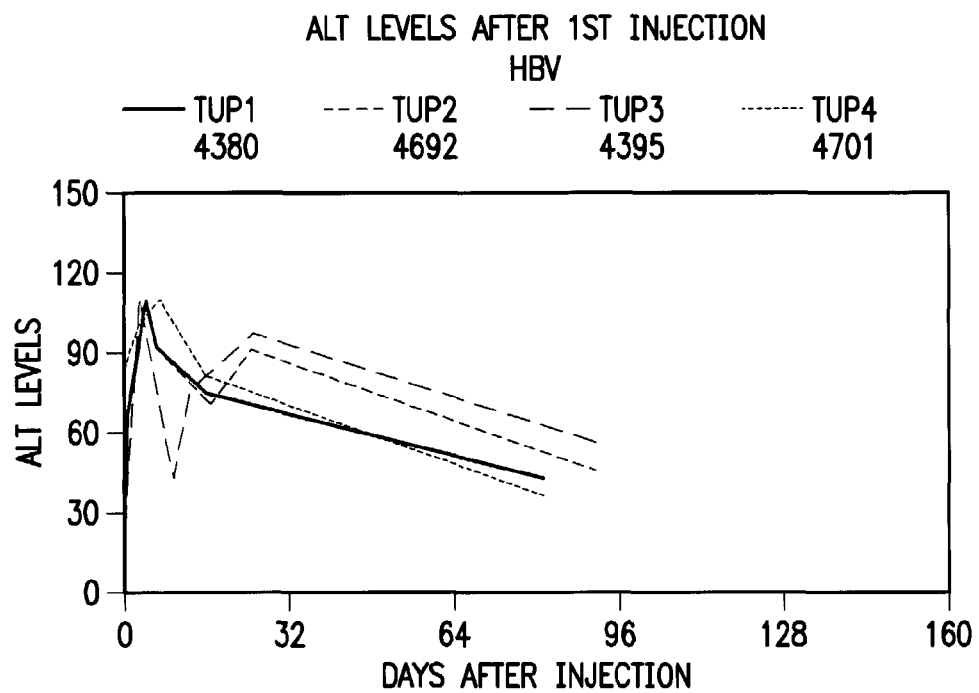
FIG. 1 shows the time course of ALT levels in *Tupaia* after HBV inoculation.

One novel aspect of the present invention is the disclosure of animal model systems where infections by human pathogens induce secondary manifestations which can be treated by therapeutic means. Animal models have been described and are well known in the art. Such therapeutric treatments may be directed towards prevention, stabilization or reversal of disease symptoms. Furthermore, these secondary manifestations in an animal model are analogous to those seen in humans after infection by the pathogen. Thus, a particularly useful animal model provided by this invention is a non-chimpanzee animal model for a human pathogen that is capable of exhibiting analogous secondary disease manifestations. The pathogens may be of viral or non-viral origin. Examples of human viruses that induce secondary manifestations in humans can include but are not limited to HBV, HCV, HIV-1, HIV-2 and HTLV-1.

A further aspect of the present invention is the ability to use such an animal model or cells, tissues or organs derived from such an animal model to identify and establish therapeutic, preventive or diagnostic products or processes for human application or use. Thus, there are provided animal models for a human pathogen that possess two-fold capability. First, the models are capable of exhibiting analogous secondary disease manifestations. Second, the models are capable of responding to therapeutic or preventive measures in the animal model to the secondary disease manifestations. The pathogen or pathogens may be viral, for example, HBV, HCV, HIV, retrovirus, and combinations thereof, or non-viral, for example, any of the pathogenic bacteria. Novel products or processes, including diagnostic products and diagnostic procedures, that have been derived from use of the present invention can be applied alone or in conjunction with other products or processes. Such animal models are also suitable for analyzing secondary disease conditions or manifestations. Therapeutic products or processes that are derived from the animal model of the present invention can include but are not limited to antibacterial or antiviral compounds, cytokines, lymphokines, immune modulation and genetic modulation including antisense and gene therapy. Therapeutic products or processes can affect replication processes of the pathogen, the secondary manifestations of infection or both. Antiviral compounds can comprise but are not limited to nucleoside analogues and other small molecules as well as proteins and other macromolecules. Immune modulations can comprise but are not limited to SIDR and GIS which have been described in co-pending U.S. patent application Ser. No. 08/808,629, filed on Feb. 28, 1997, incorporated by reference herein. Compounds or treatments that have been characterized by screening in the animal model of the present invention can later be applied to human disease caused by such pathogens. Diagnostic products or processes that derive from the present invention can include but are not limited to DNA and RNA sequences that are associated with disease. Diagnostic products or processes that derive from the present invention can also include assays for the detection of the presence or amounts of particular lymphokines, cytokines, antigens, epitopes of antigens, antibodies or other biological macromolecules that may be asociated with a disease state. Thus, the present animal models are useful for treating or preventing human pathogens. The present invention also allows the analysis and study of primary and secondary disease manifestations in the small animal model to investigate the development of pathogenic processes either passively by observation of these processes or actively studying them by selectively interfering in these processes.

The present invention provides a lower primate as an animal model for human retrovirus infection. This invention also provides a primate as an animal model for human retrovirus infection, such primate not including or excluding any members of the primate order Anthropoidea. As described above, the human retrovirus may comprise Human Immunodeficiency Virus (HIV), including HIV 1, HIV 2. The human retrovirus may also comprise Human Lymphotrophic T-Cell Leukemia (HTLV), including HTLV-I and HTLV-II.

In one aspect of the present invention, it has now been discovered for the first time that the *Tupaia* small animal model is a useful model for HBV infection since it exhibits not only infectivity by HBV but also pathological manifestations that are secondary to the viral infection similar to what is seen in humans. It is also disclosed that in this small animal model, the secondary manifestations are amenable to a therapeutic treatment such that they are able to be prevented or reversed.

In another aspect of the present invention, it is disclosed that *Tupaia belangeri* is suitable as a host for HIV infection. Although higher primates such as chimpanzees, monkeys, and gibbons have been studied as hosts for retroviruses, this aspect of the present invention is the first disclosure that a primate that is not a member of the sub-order anthropoidea can be a suitable host for a human retrovirus. In addition to HIV-1, other human retroviruses may also be used with the animal model of the present invention. These can include but are not limited to HIV-2, HTLV-I and HTLV-II. Previous to the present invention, the systems in current use all have drawbacks in terms of finding effective modes of establishing therapeutic regimes for HIV infections in humans. The first system used to investigate the life cycle of HIV virus, in vitro tissue culture, intrinsically lacks features of the disease that are important in the disease process. These include a lack of interaction with an immune system and the absence of physical structures such as lymph nodes. This system also lacks the population of numerous cell types that constitute the blood and lymph systems. The chimpanzee has been used a subject for in vivo studies. However, this animal is an endangered species and in addition it is a very expensive system that necessitates a long-term maintenance of potentially infectious animals. An attempt at an in vivo small animal model has been attempted by the creation of nude mice that have human lymphocytes implanted in them. However, this is not a natural infection since the model with implanted human cells is by its nature unable to have any appreciable immune system. In addition, this is not really a small animal model for disease since only the implanted human cells can be infected by HIV and there is a lack of pathology in any other cells or organs of the mouse.

In this aspect of the present invention, *Tupaia belangeri* is disclosed as a novel animal model that is superior to the ones presently being used. *Tupaia* are small animals which are cheaper and easier to maintain than chimpanzees. They also have shorter lifespans, making it easier to increase the number of subjects through breeding programs. The short life span also accelerates many of the biological processes of the animal thereby speeding up the output of experimental data.

Additionally, they are not considered to be endangered and *Tupaia belangeri* as well as other memberrs of the *Tupaia* genus are found in a wide geographic area of Asia. This aspect of the present invention provides a small animal model for infection by human retroviruses that can be used for screening therapeutic regimens for blocking viral replication in this host. It also provides a means for identifying products and processes useful in therapetic treatment of viremia, including transient viremia and/or chronic viremia, and/or secondary manifestations that may be a result of infection by human retroviruses.

Cells, tissues or organs derived from any of the animal models of the present invention are usefully provided herein.

The examples that follow are given to illustrate various aspects of the present invention. Their inclusion by no means is intended to limit in any way the scope of this invention as more particularly defined by the claims.

DESCRIPTION OF THE PREFERRED EMBODIMENTS

Example 1

Infection of *Tupaia belangeri* with HBV

The present example is a demonstration that a primate not belonging to the suborder Anthropoidea, such as *Tupaia belangeri*, can be infected with a human virus (HBV) such that the symptoms that are displayed in this animal model correspond to the pathology and symptoms of the natural human infection.

Materials and Methods

Subjects. *Tupaia belangeri* were obtained from Duke University Vivarium, Durham N.C., and housed at Albert Einstein College of Medicine, Animal Institute. *Tupaia* were housed at 70 degrees in 12 hour light/dark cycles, one or a mating pair of two shrews per cat cage or squirrel monkey cage, and given a diet of fresh fruit (grapes, banana, apple, and orange), dried cat food, and water. Each cage also contained a small nest box.

HBV infection of *Tupaia*. *Tupaia* were anesthetized using ketamine:xylazine at 94:1 (Ketaset at 100 mg/ml from Fort Dodge Animal Health, Fort Dodge, Iowa and Rompum at 20 mg/ml, from Bayer, Shawnee Mission, Kans.) administered by intramuscular injection into the thigh, at a dose of 0.001 ml/gm body weight. HBV inoculations were derived from a pool of ten HBV serpositive clinical specimens. For infection, the tail of a *Tupaia* was shaved and disinfected followed by intravenous injection of 0.1 ml of the HBV pool into the tail vein using a 27 gauge butterfly needle.

Serology. After shaving and disinfecting the underside of the tail, blood samples of 0.5 to 1.0 ml were collected using 27 gauge butterfly needles, from the tail vein of anesthetized *Tupaia*. Blood samples from *Tupaia* were collected before HBV innoculation and weekly thereafter. All HBV serological tests performed at ENZO Clinical Laboratories (Farmingdale, N.Y.) by the same procedures that are used for clinical specimens except for a series of samples from longterm infections where a polyclonal HBsAg test was used (Austral Biologicals, San Diego, Calif.). Serial dilutions of plasma in PBS were made to titer the *Tupaia* antibody levels to the informative range of the test. In one case where a long term ALT (alanine aminotransferase) levels were measured by a commercial kit purchased from Sigma (St. Louis, Mo.) using the manufacturers directions.

Histology. Liver percutaneous biopsies were performed under general anaesthesia using sterile techniqes. A small vertical midline incision in the abdomen was used to expose the liver, a small wedge liver biopsy was removed after tying off a portion of the liver with a purse line suture using a taper needle and silk. Biopsy tissues were split: one portion was preserved in neutral formalin, and the other was frozen at −80° C. Formalin-fixed tissue was parafin embedded, sectioned, and stained with hematoxylin/eosin (H&E stain) for histological examination, trichrome stain for collagen, or reticulin stain, which stains *Tupaia* collagen.

In situ PCR amplification and detection of HBV RNA. Reactions were carried out according to the protocol described in Liu et al., (1997; J. Vir. 71:4079) except that HBV specific sequences for primers and probe were used. The sequences for these is as follows:

```
HBV A:
5'-TGCCTGAGTGC(TA)GTATG-3'      (SEQ ID NO: 1)

HBV B:
5'-TAGGAGGCTGTAGGCAT-3'         (SEQ ID NO: 2)

HB Probe:
5'-TTTATAAGGGTCGATGTCCAT-3'     (SEQ ID NO: 3)
```

Results

HBV infection of *Tupaia*. Evidence for the HBV infection of *Tupaia* innoculated with HBV carrier sera is shown in Table 1 below.

TABLE 1

| HBV antigens in Tupaia: serological evidence of infection | | | | | | |
|---|---|---|---|---|---|---|
| Antigen/ Animals | Pre- infection | 5 min | 2 hr. | 24 hr. | 4 days | 10 days |
| A.S-Ag | | | | | | |
| 1 | − | − | + | + | + | − |
| 2 | − | − | nt | + | + | − |
| 3 | − | nt | nt | nt | + | − |
| 4 | − | nt | nt | nt | + | − |
| | Pre- infection | 6 days | 9 days | 17 days | 24 days | 60 days |
| B.E-Ag | | | | | | |
| 5 | − | − | + | + | + | − |
| 6 | − | − | − | + | + | − |
| 7 | − | − | − | − | + | − |

In HBV infected *Tupaia*, HBV surface antigen (HBsAg) was detected beginning at 2 hours after innoculation, peaked at 24 to 48 hours, and persisted for 4 to 6 days in all treated *Tupaia*, Table 1a. HBsAg production from longer timepoints were negative with the monoclonal assay. However, when a polyclonal antibody kit was substituted, HbsAg continued to be detected throughout the course of the time of the study (10 months). E-antigen, also known as HBeAg, is the serum soluble modification of viral core protein and, in man, the marker for active viral replication. HBeAg was detected in blood samples from all three *Tupaia* tested after HBV innoculation, Table 1b. Detection of HBeAg secretion extended from 9 to 24 days in consecutive blood samples. In control untreated *Tupaia*, no HBV viral antigens were detected in the blood. Similarly, in pretreatment blood samples from HBV innoculated *tupaia*, no HBV was detected, indicating that the *Tupaia* used had no previous exposure to human HBV. From this serological data we conclude that the *Tupaia* innoculated with HBV carrier sera were infected, and that they replicate virus.

Immunological response of *Tupaia* to HBV antigens. Since the host immune response to HBV is an important component in the necroinflammatory reaction in infected human liver, the ability for HBV antigens to invoke an immune response in *Tupaia* was tested. Plasma antibody levels to HBV viral proteins were measured after infection of *Tupaia* as a measure of the humoral immune response to HBV. Antibodies dircted against HBsAg were not detected in untreated *Tupaia*, nor in blood samples taken from the *Tupaia* prior to their inoculation with HBV. The results are shown in Table 2 below.

TABLE 2

Antibody levels after HBV inoculation

| week | Tupaia-1 | Tupaia-2 | Tupaia-3 |
|---|---|---|---|
| 0 | 10 | 10 | 10 |
| 4 | 10 | 10 | 4550 |
| 7 | 10,000 | 110 | 7000 |
| 12 | 3,050 | 24,500 | 220,000 |

As shown in Table 2 below, detection of antibodies took place at different times for each of the subjects. One animal produced detectable levels after only 4 weeks. A second subject produced detectable levels beginning 7 weeks after infection. All three subjects were inoculated a second time with HBV. When tested all three subjects were positive for antibodies with titers that varied between $2 \times 10^3$ to $2 \times 10^5$ for individual HBV infected *Tupaia* after the booster response. These results shown that after HBV infection, *Tupaia* are able to produce a humoral immune response to the virus. The variablity in timing and magnitude of antibody production is similar to that seen among human patients.

Hepatocyte death in HBV infected *Tupaia*. In HBV-infected human liver tissue, the host cellular immune response to virally infected hepatocytes is thought to cause hepatocyte death. One marker of hepatocyte death is the release of amino transferases from lysed hepatocytes into the plasma. Alanine amino transferase (ALT) levels in plasma are a standard measure of hepatocyte death and liver injury in viral hepatitis. ALT levels in *Tupaia* plasma were determined before and after inoculation of *Tupaia* with HBV. Normal, untreated *Tupaia* ALT levels ranged from 13 to 40 units/ml, and average 25 units/ml, similar to normal human ALT levels. However, following HBV innoculation, ALT levels in *Tupaia* were elevated two to five fold over normal levels as shown in FIG. 1. This rise can be considered to be an indication that as seen in humans, there have been cellular immune responses to HBV that have led to hepatocyte death. The duration of ALT elevation varied between individual *Tupaia*, in the most extreme case persisting for 10 months. Persistant or periodic ALT elevation over 6 months or longer time period is a characteristic of chronic hepatitis in humans where there is a continuous cycle of hepatocytes being infected and destroyed.

Histological Evidence of Hepatitis and HBV Replication.

Figure 2:
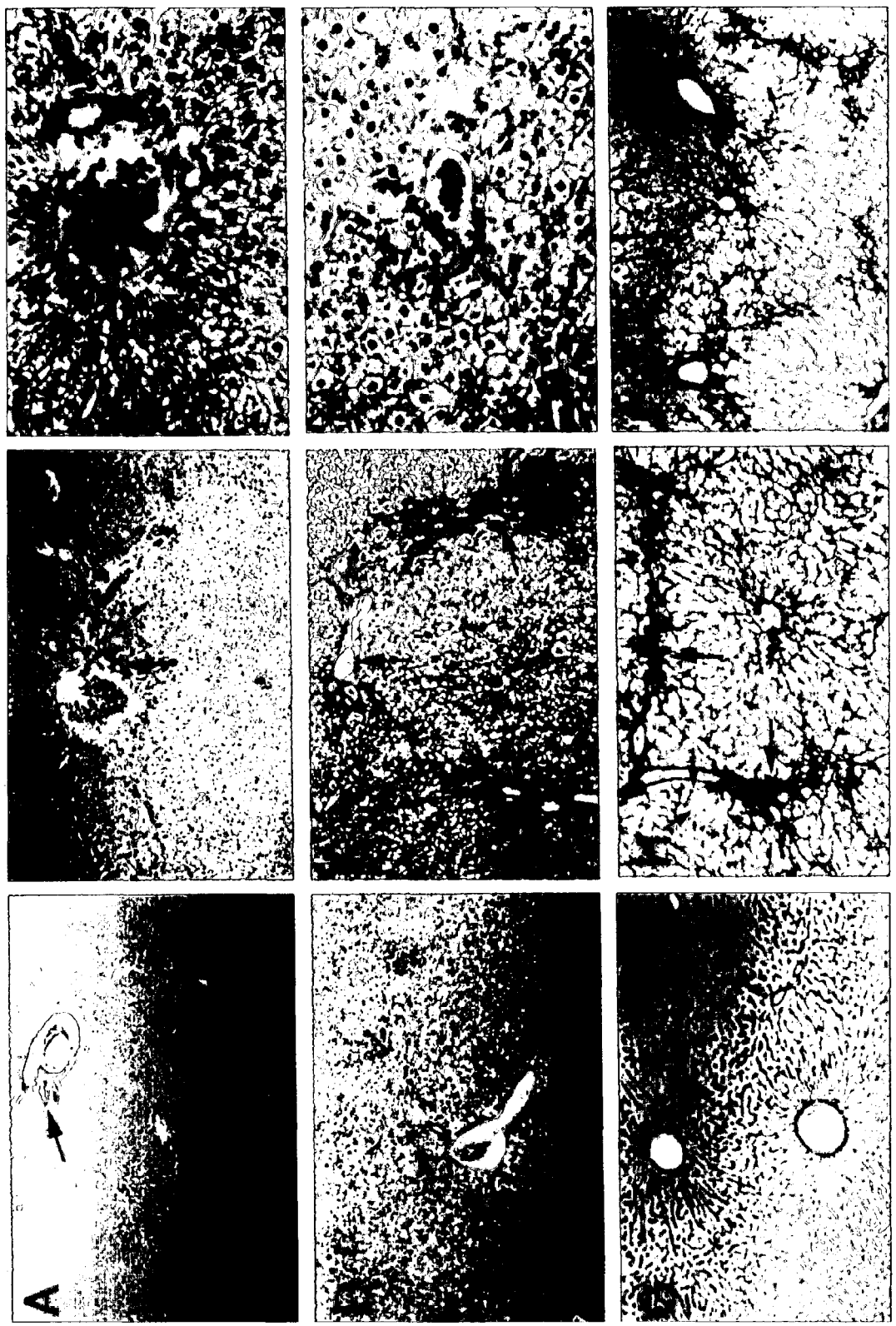
FIG. 2 are photomicrographs illustrating liver histomorphology of normal and HBV-infected *Tupaia*.

Exemplary microphotographs of biopsies from infected and uninfected *Tupaia* are shown in FIG. 2.

Panel A: Untreated normal *Tupaia* liver section stained with hematoxylin ane eosin (50×) shows unremarkable morphology, with a single bile duct adjacent to the portal vein, and occasional lymphocytes. The liver structure is comparable to normal human liver.

Panel B. HBV-infected *Tupaia* liver section from a biopsy taken 2 months after HBV infection. H/E stain shows bile duct proliferation (50×). The field shown is representative of many fields viewed on this and adjacent sections of liver tissue.

Panel C. HBV-infected *Tupaia* liver section from a biopsy taken 2 months after HBV infection and stained with H/E (250×) shows altered hepatocyte morphology. Some cells are enlarged in size (balooning). Portal inflammation and mononuclear cells around the portal vein are seen.

Panel D. HBV-infected *Tupaia*, 10 month biopsy, liver section stained with H/E (50×) shows periportal and lobular lymphocyte infiltration.

Panel E. HBV-infected *Tupaia*, 6 months biopsy, liver section stained with trichrome (50×). Liver architecture is distorted by strands of collagen in this field. Strands of blue staining collagen are seen which connect at least three portal zones. Full formed cirrhotic nodules are not seen.

Panel F. HBV-infected *Tupaia*, same animal as in Panel D, 10 month liver biopsy stained with H/E (250×). Lymphocytes extend from the portal triad and surround degenerating hepatocytes in a piecemeal necrosis pattern.

Panel G. Uninfected *Tupaia* liver section stained with reticulin shows normal architecture, a network comparable to normal human liver.

Panel H. HBV-infected *Tupaia*, same animal as in Panel E, 6 months after HBV infection, stained for reticulin, shows groups of hepatocytes not individually surrounded by reticulin indicating regeneration, and thick strands of extracellual matrix indicating collagen deposition and hepatocellular collapse.

Figure 3:
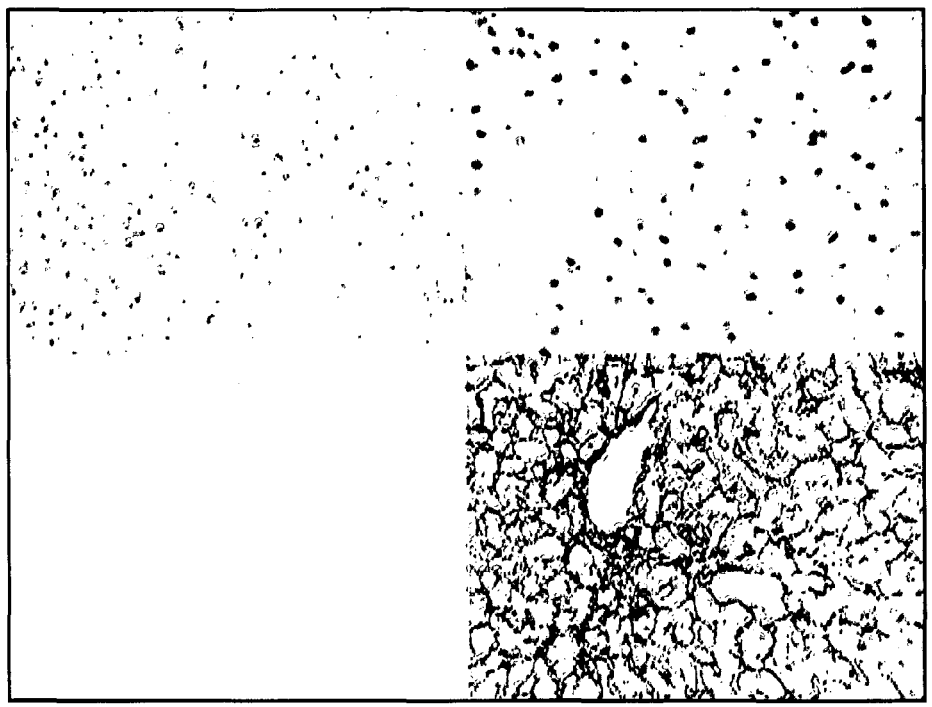
FIG. 3 are photomicrographs taken of *Tupaia* liver sections after in situ PCR amplification and detection of HBV RNA

In situ PCR amplification and detection of HBV RNA is shown in FIG. 3. The upper left panel shows the distribution of hepatitis B RNA in the liver of a *Tupaia*, 6 months after infection by HBV. At higher magnification, (upper right panel) one can see infected hepatocytes and occasional Kupffer cells. Viral RNA was not detected in an uninfected control animal, as seen in the lower left panel of FIG. 3. The corresponding reticulin stain of the virally infected liver shows a diffuse increase in reticulin fibers in the region of the portal tract extending to the region of the central vein (lower right panel of FIG. 3).

Summaries of three *Tupaia* cases are presented in more detail below; one control *Tupaia* that was uninfected and the two *Tupaia* that were examined at 6 months and 10 months after inoculation with HBV. Liver sections from each specimen were stained and then analyzed independently by two clinical pathologists.

*Tupaia* #1 Untreated adult *Tupaia*. The H&E stain demonstrates normal hepatic architecture. There is no evidence of inflammation in the portal tracts and there are rare mononuclear cells in the sinusoidal spaces. Hepatocytes and bile ductules are unremarkable. The reticulin stain, which stains for collagen deposition, does not show any increased reticulin. Hence, this liver tissue is within normal limits. No evidence was seen for the presence of HBV RNA after an in situ PCR reaction.

*Tupaia* #2. Specimens obtained 6 months after inoculation with HBV. The H&E stain demonstrates normal hepatic architecture. There is widespread evidence of moderate, chronic inflammation in the portal tracts (portal hepatitis). The majority of these inflammatory cells are lymphocytes and plasma cells. Occasionally, the inflammation goes past the limiting plate (lobular hepatitis), although hepatocyte necrosis/piecemeal necrosis is not evident. There are scattered mononuclear cells in the sinusoidal spaces. The hepatocytes show a diffuse and severe steatosis (fatty change). Serological tests gave negative results for HCV, indicating that in this *Tupaia* the steatosis did not result from contaminating or previous HCV infection. Rare ground glass cells are evident, which is a common finding in HBV infected human liver and results from HBsAg accumulation within hepatocytes. The reticulin stain for collagen deposition shows a diffuse and moderate increase in reticulin fibers centered at the portal tracts and rarely extending to the region of the central vein. These histologic findings are consistent with moderately severe, chronic viral hepatitis. In results of tests for HBV replication in adjacent tissue sections, viral RNA was detected in occasional hepatocytes using the RT in situ PCR technique. The viral nucleic acid localized to the region of the nuclear membrane. This demonstrates active HBV replication in the liver at the time of biopsy.

*Tupaia* #3. Specimens obtained 10 months after inoculation with HBV. The H&E stain demonstrates normal hepatic architecture. There is minimal evidence of chronic inflammation in the portal tracts (portal hepatitis). There are rare mononuclear cells in the sinusoidal spaces and the hepatocytes are unremarkable. The reticulin stain for collagen shows a focal and mild increase in reticulin fibers centered at the portal tracts, indicating deposition of fine strands of connective tissue (periportal fibrosis). These histologic findings are consistent with mild, chronic hepatitis. Viral RNA was not detected at the time of biopsy (10 months post innoculation).

Summary: A lower primate or a primate not belonging to the suborder Anthropoidea, *Tupaia belangeri*, can be infected with HBV such that a number of characteristics that parallel human infection can be observed. These disease symptoms are useful markers for determining the effectiveness of a therapeutic process. Some of these markers, such as the presence of HBeAg, can be used to monitor the presence of an ongoing viral replication. Other markers, such as ALT levels and histological examinations for inflammatory responses can be used for the determination of the extent of secondary manifestations of infection.

Example 2

Effects of Induction of Oral Tolerization on HBV Infection of *Tupaia*

This example is a demonstration that *Tupaia belangeri* can be used as a model of therapeutic processes as well as infection processes. Secondary disease manifestations that are similar to those seen in humans are alleviated by induction of oral tolerance to HBV antigens. This example demonstrate that oral administration of viral antigens can down regulate a pre-existing humoral immune response to HBV infection and can prevent induction of a booster response to an HBV rechallenge. This example also demonstrates that induction of oral tolerance prior to infection dramatically down regulates or even eliminates the immune response to the viral infection.

Materials and Methods

Subjects, Serology, and Histology were as described in Example 1 above.

Induction of Oral Tolerization: Adult *Tupaia* were fed 30 ng of HBsAg in a solution containing 1 mg fetal bovine serum carrier (10 doses, given every other day), before or after infection with HBV-infected human serum. HBsAg used as the tolerant was derived from the cell culture supernatant collected from human hepatocyte cell line IHBV6.7. The derivation and characterization of this cell line has been described above in Example 1 of U.S. Ser. No. 08/876,635, filed on Jun. 16, 1997, incorporated by reference herein. At confluence, IHBV6.7 stationary cells produce 90 ng/ml HBsAg. For no treatment controls, adult *tupaia* were fed 1 mg BSA without the HBsAg.

Results

Figure 4:
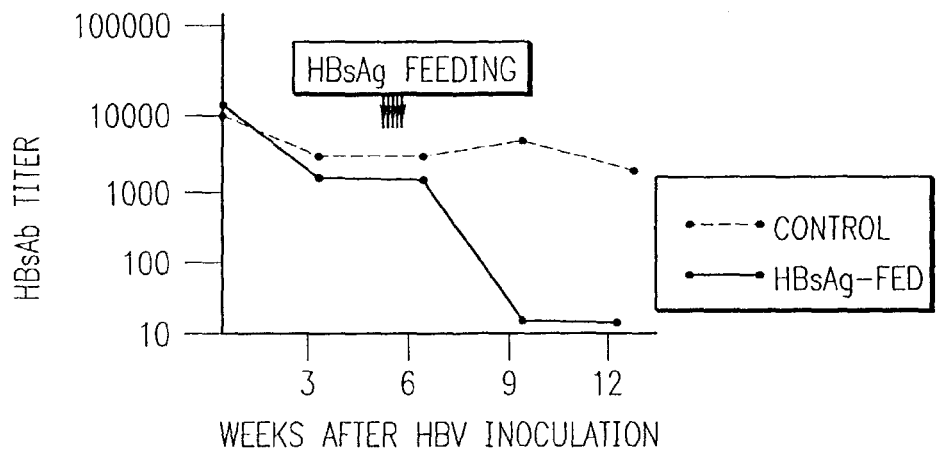
FIG. 4 is a time course that shows the effects of post-infection oral tolerization on the levels of antibodies to HBV antigens.
Figure 5:
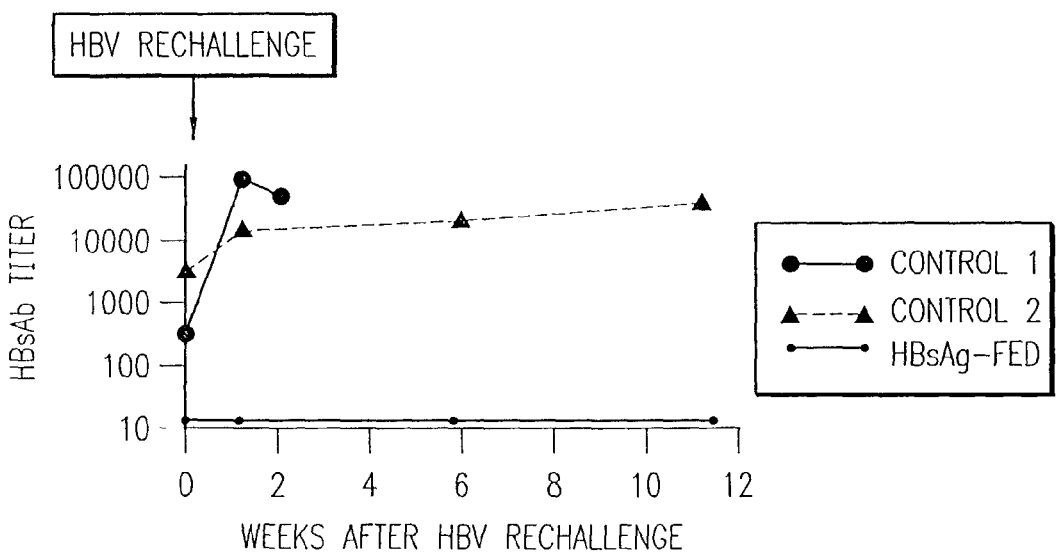
FIG. 5 illustrates the effects of oral tolerization on the levels of antibodies to HBV antigens after HBV rechallenge.

Antibody levels: When a pair of *Tupaia* were infected with HBV, high levels for antibodies to surface antigen were detected (FIG. 4). When one of the infected *Tupaia* was orally administered HBsAg 6 weeks post-infection, antibody levels were reduced by at least two orders of magnitude while the control continued to produce high levels of antibody. When these two animals were given a second inoculation the control subject showed a booster response as did a second control animal (FIG. 5). However, the subject that had been orally tolerized as previously described failed to demonstrate any response to the HBV challenge. No detectable levels of HBV antibody were detected over a twelve week period.

Figure 6:
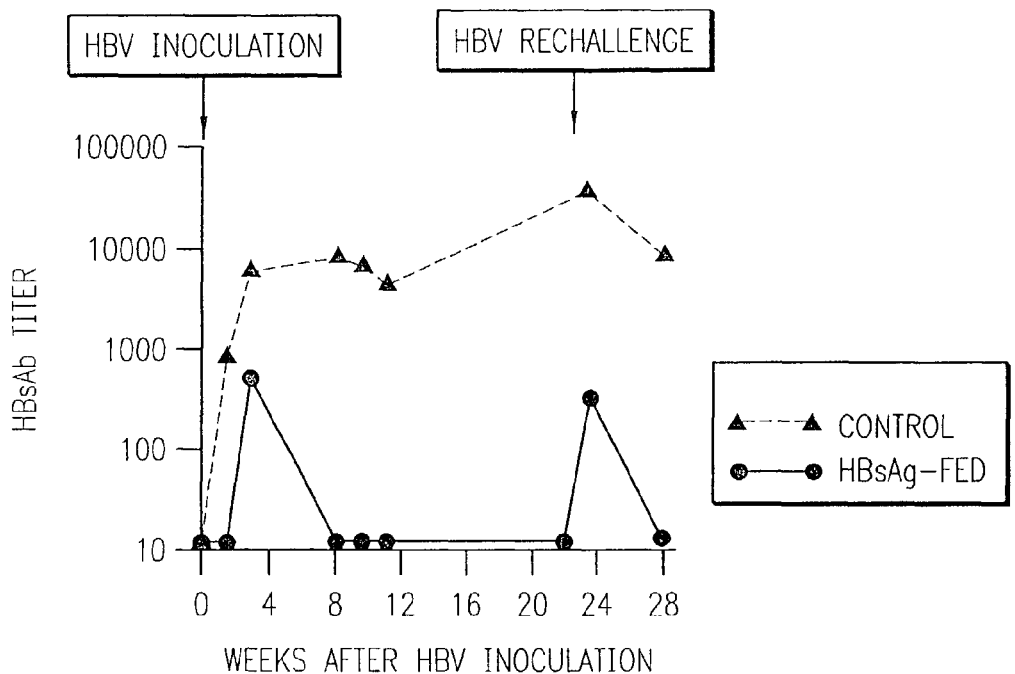
FIG. 6 shows the effects of pre-infection induction of oral tolerization on the levels of antibodies to HBV antigens.

*Tupaia* were also tolerized prior to HBV infection. Results from this experiment are shown in FIG. 6. The subject which was treated by oral administration of HBsAg showed an initial response that was 10 fold lower than the control. When tested at 8 weeks post-infection, antibody levels in the tolerized animal were undetectable and remained so until a rechallenge was administered at 21 weeks post infection. After rechallenge, antibody level response was 400 fold lower in the tolerized animal compared to the control. It also soon returned to undetectable levels.

Figure 7:
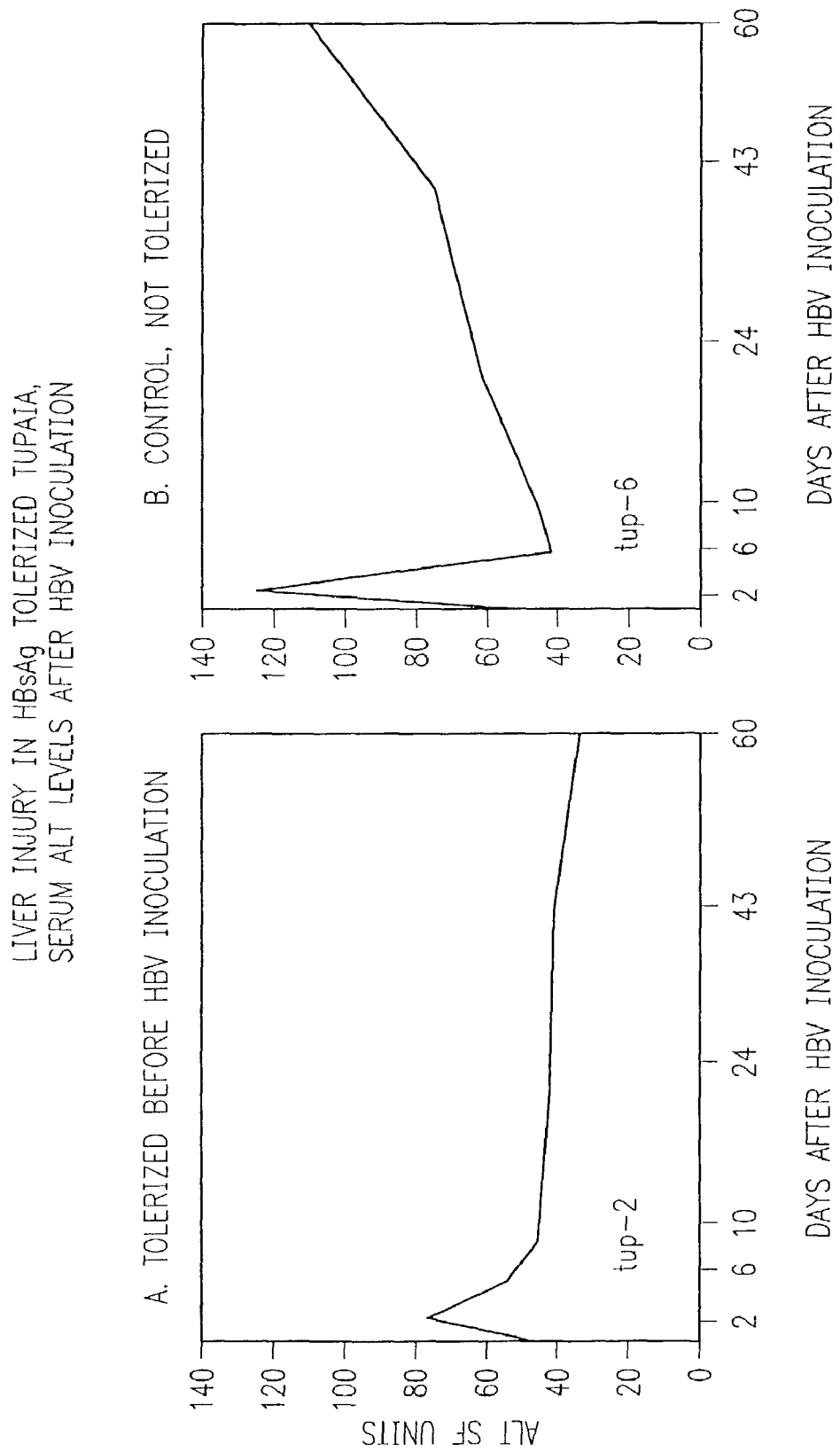
FIG. 7 shows the effects of pre-infection induction of oral tolerization on HBV induced liver damage as determined by serum ALT levels.

ALT Levels: The subjects shown in FIG. 6 were also tested for liver injury by measuring serum ALT levels. Results of these assays are shown in FIG. 7. For both the tolerized and the control *Tupaia*, initial ALT peaks seen at two days post-inoculation return to normal levels within ten days. In the control animal, the ALT starts to rise again from day 24 to 60 days post-inoculation which is diagnostic of continuing liver damage. In contrast, the tolerized subject maintained normal levels of ALT throughout the study.

Figure 8:
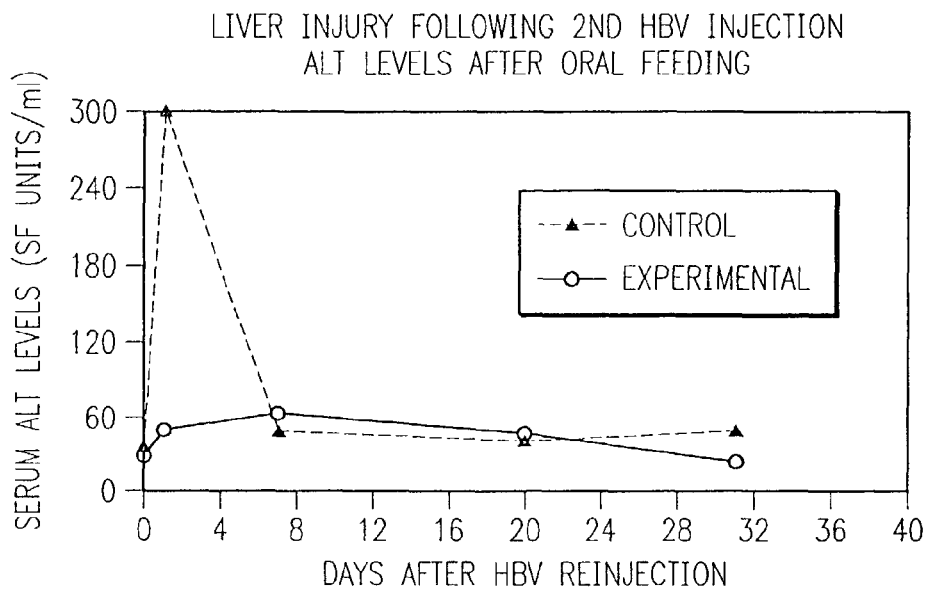
FIG. 8 shows the effects of oral tolerization on HBV induced liver damage after HBV rechallenge.

The subjects shown in FIG. 5 who had booster HBV injections were also tested for liver injury by measuring serum ALT levels. Results of these assays are shown in FIG. 8. The control HBV infected *Tupaia* shows a high ALT response to the second inoculation whereas the subject treated with oral tolerization demonstrates alsmost no response.

Figure 9:
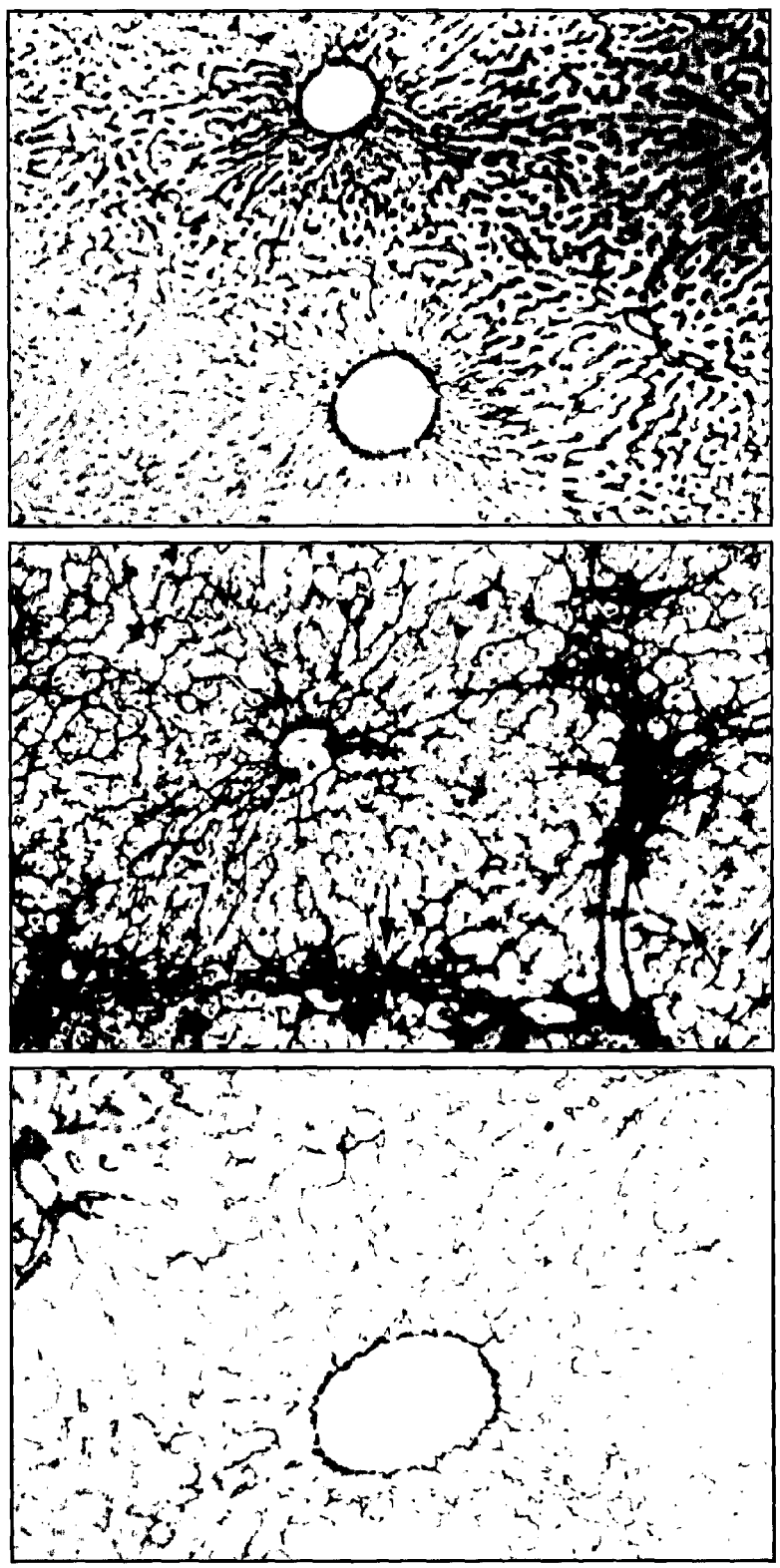
FIG. 9 are photomicrographs of *Tupaia* liver biopsy specimens that have been stained for reticulin.

Histology: Liver biopsies from 3 HBV-infected, BSA-fed controls showed varying degrees of inflammatory and fibrotic lesions, (FIG. 2). In contrast 2 HBsAg-fed infected *Tupaias* and 3 uninfected *Tupaias* were lacking evidence of inflamation or fibrosis. An example of these are shown in FIG. 9 where the top panel shows normal liver specimen from an uninfected *Tupaia*. In contrast, the middle panel shows the unhealthy tissue seen in a specimen form a *Tupaia* infected with HBV. The arrows in the middle panel show the extensive fibrosis present 10 months after infection. The lower panel demonstrates the absence of any signs of a disease process 10 months after infection in a *Tupaia* which has undergone post-infection oral tolerance induction.

Summary

The foregoing example demonstrates that HBV infection of *Tupaia belangeri* can be used as a model sytem for investigating therapeutic processes. In this example, oral tolerization to HBV antigens ameliorated hepatic inflammation. Contrary to what may be expected, the abrogation of an immune response to an HBV surface antigen did not lead to a fulminant display of viremia. When the *Tupaia* were tolerized to the surface antigen of HBV prior to infection, there was a dramatic decrease in the levels of antibody to the surface antigen. In addition, a therapeutic effect was noted in terms of a loss of inflammatory responses to the HBV infection that had been observed in the livers of the non-tolerized animals. This effect will allow a therapeutic regime in this and other pathogen systems where oral tolerization can be carried out with regard to selected antigens or epitopes that invoke a self-immune response while sustaining an immune response to other antigens or epitopes. This would allow a natural control of the infection by the subject.

Example 3

Infection of a Lower Primate by a Human Retrovirus

In one aspect of the present invention, a novel primate model not belonging to the suborder Anthropoidea is disclosed for the development of therapies for the treatment of infection by human retroviruses. In this aspect of the invention, lymphocytes from *Tupaia belangeri* are shown to be capable of being productively infected by HIV. This animal model enjoys the advantages being non-endangered, easily grown and cared for and has a rapid generation time.

Materials and Methods

Subjects. *Tupaia belangeri* were obtained and maintained as described in Example 1 above.

Blood Collection. Two adult *Tupaia* were anesthetized as described in the previous example. The underside of the tail was shaved and disinfected, and blood samples of 1.3 ml were collected using. 27 gauge butterfly needles, into EDTA collection vials.

Peripheral blood lymphocyte culture. Whole blood was centrifuged at 500×g for 10 minutes to separate plasma from cells. Plasma was taken off and the remaining cell fraction was diluted with an equal volume of sterile PBS and layered over 1.3 ml of Histopaque 1077 (Sigma, St. Louis, Mo.). The cells were centrifuged 30 min at 500×g at room temperature. The upper layer was discarded and the opaque layer of mononuclear cells was collected and washed 2× with 15 ml sterile PBS. The cell pellet was resuspended in 1 ml of RPMI, 10% FBS with Penn/Strep added (Gibco/BRL, Gaithersburg, Md.)) and plated in 96 well tissue culture plates at 0.2 ml per well.

HIV infection. Cultures in some wells were stimulated by exposure to 0.1 ug of Phytohemagglutinin (PHA) (Sigma, St. Louis, Mo.) for 2 hours at 37° C. prior to infection. Cells were grown in the media above supplemented with 30 units/ml of IL2 (Boehringer-Mannheim, Indianopolis, Ind.). HIV used for infection was CR10/T (NIH Reference Program) and amounts were estimated by measurement of p24 using a commercially available kit (NEN, Boston, Mass.). Infection was carried out by the addition of 0.001 pg/well followed by incubation at 37° C. for two hours. Supernatants were then taken off and 200 μl of media was added to each well.

Infection analysis. Cell population numbers at various times after infection were determined by use of a hemocytometer. Viral synthesis was determined by measurement of p24 production as described above.

Results

The starting number of cells from the two *Tupaia* donors differed by a factor of 10 so most measurements were made with the PBLs from only the *Tupaia* with the higher cell numbers. The p24 measurements at various time points after infection are shown for this *Tupaia* in Table 3 below.

TABLE 3

HIV-p24 production in Tupaia PBL cultures

| Expt. | Infection | 5 days | 8 days | 11 days | 14 days |
|---|---|---|---|---|---|
| 1. | +HIV | >2 | >2 | 95 | 5.7 |
| 2. | −HIV | 0.3 | NT | 0.19 | 0.13 |
| 3. | +HIV | >2 | >2 | 9.7 | 5.7 |
| 4. | −HIV | NT | 0.4 | NT | NT |

Cells in Experiments 1 and 2 were cultured in the presence of T-cell growth stimulator PHA; cells in experiments 3 and 4 were cultured without stimulation.

In the ELISA assay the samples from 5 and 8 days post-infection were used undiluted and gave saturation values for the HIV infected cells with this assay. Uninfected cells gave readings that were essentially background. At the later time points of 11 and 14 days, serial 1:10 and 1:100 dilutions of the samples were used to obtain more accurate readings and then extrapolated back to values for undiluted samples. These are also shown in Table 3 and give values that are 40 to 500 times as high as the background level seen in the uninfected cells. Lower cell numbers after 14 days (data not shown) may be responsible for the drop-off in p24 levels compared to the 11 days post-infection samples. The infected cells from the second *Tupaia* that had lower cell numbers gave essentially the same results as those shown in Table 3 for the 5 and 8 day samples showing that cells from this animal were also capable of sustaining HIV infection. In conclusion, it can be seen that HIV is able to mount a vigorous infection and maintain a state of viremia up to 14 days after infection of PBLs derived from the *Tupaia* animal model. These results also demonstrate that there is no necessity to stimulate the PBLs with PHA to achieve viral infection.

Many obvious variations will be suggested to those of ordinary skill in the art in light of the above detailed description and examples of the present invention. All such variations are fully embraced by the scope and spirit of the invention as defined more particularly by the claims that follow.

What is claimed is:

1. A method for developing a therapeutic procedure in a model animal system comprising the steps of:
   a) infecting a *Tupaia belangeri* with hepatitis B virus (HBV);
   b) carrying out a potential therapeutic procedure in said infected *Tupaia belangeri*; and
   c) evaluating the effect of said potential therapeutic procedure on a disease manifestation caused by said HBV in said infected animal, wherein said disease manifestation is hepatic histological evidence of fibrosis, bile duct proliferation, lymphocytes, ground glass hepatocytes or a combination thereof.

2. The method of claim 1 wherein said potential therapeutic procedure comprises oral tolerization.

* * * * *

UNITED STATES PATENT AND TRADEMARK OFFICE
CERTIFICATE OF CORRECTION

| | | |
|---|---|---|
| PATENT NO. | : 8,012,456 B2 | |
| APPLICATION NO. | : 10/042711 | |
| DATED | : September 6, 2011 | |
| INVENTOR(S) | : Jennifer June Brown et al. | |

It is certified that error appears in the above-identified patent and that said Letters Patent is hereby corrected as shown below:

On the title page under item (63) Related U.S. Application Data, --continuation of application No. 09/356,293, filed on Jul. 16, 1999 which is a-- should be inserted before "continuation-in-part of application No. 08/876,635, filed on Jun. 16, 1997, now abandoned."

Signed and Sealed this
Twenty-eighth Day of June, 2016

Michelle K. Lee
*Director of the United States Patent and Trademark Office*